United States Patent [19]
Swisher, III

[11] Patent Number: 5,527,283
[45] Date of Patent: Jun. 18, 1996

[54] SAFE MEDICAL SYRINGE AND METHOD OF MANUFACTURE

[76] Inventor: Kyley Swisher, III, 14612 Mustang Path, Glenwood, Md. 21738

[21] Appl. No.: 843,247

[22] Filed: Feb. 28, 1992

[51] Int. Cl.$^6$ .............................. A61M 5/50; A61M 5/32
[52] U.S. Cl. ............................................... 64/110; 604/195
[58] Field of Search ..................................... 604/192, 110, 604/195, 196

[56] References Cited

U.S. PATENT DOCUMENTS

| | | | |
|---|---|---|---|
| 4,804,370 | 2/1989 | Haber et al. | 604/195 |
| 5,171,300 | 12/1992 | Blake, III et al. | 604/110 |
| 5,215,533 | 6/1993 | Robb | 604/195 |
| 5,263,934 | 11/1993 | Haak | 604/110 |

FOREIGN PATENT DOCUMENTS

| | | | |
|---|---|---|---|
| 9014119 | 11/1990 | WIPO | 604/195 |
| 9108788 | 6/1991 | WIPO | 604/195 |

*Primary Examiner*—John D. Yasko
*Assistant Examiner*—Adams J. Cermak

[57] ABSTRACT

Disposable medical syringe 10, consisting of a hollow syringe chamber 12, for receiving a piston 14, traversing a displaceable extendible path 16, in the chamber, a rod 18, axially coupled to one end of the piston 14, and at the other end to a thumb engaging surface 20, a stop member 22, in the hollow chamber 12, at a proximal end and adjacent to the rod 18 for terminating one end of the displaceable extendible path 16, a cap 30, securely but removably mounted at a distal end of the hollow chamber from the one end and having a tubular coupling 32, for receiving in frictional engagement a syringe needle 34, a supporting body for axially centering support of the needle within the hollow chamber and securely mounted to an inner end of the needle 34, a distal end of the needle 34, adapted for injection in a patient for serving to pass fluid received from the hollow chamber to pass into the patient, an annular projection 38 disposed about the tubular coupling 32, for latch-engaging the distal end of the needle therein, and a snap-socket fastener arrangement 50, consisting of one receiving-female portion 52, and one snap-fit-engaging male portion 54, fastening thereto, either the one or the other portions included on an end of the piston proximal the support body, and the other of the one or the other portions included on an end of the support body proximal the piston.

10 Claims, 1 Drawing Sheet

SAFE MEDICAL SYRINGE AND METHOD OF MANUFACTURE

BACKGROUND OF THE INVENTION

1. Field of the Invention

The invention relates to a safely disposable, singly-usable medical syringe 10, wherein, after its use for injecting serum or the like into a patient by a doctor-technician or similar others using the syringe, the needle 34, is automatically pressure interlocked and connected to the syringe plunger 14, and withdrawn into the interior body of the syringe 10, preventing any further and unintended and unprofessional uses or unintended needle stick injuries. More particularly, the invention is directed to a disposable medical syringe 10, consisting of a hollow syringe chamber 12, for receiving a syringe plunger or piston 14, which piston traverses a displaceable extendible path 16. Within the syringe chamber 12, a rod 18, is axially coupled to one end of the piston 14, and at the other end is formed into a thumb engaging surface pad 20. A stop member 22, is located in the hollow chamber 12, at a proximal end and adjacent to the rod 18, which terminates one end of the displaceable extendible path 16. A cap 30, is securely but may be removably mounted at the distal end of the hollow chamber 12. A tubular coupling 32, for receiving in frictional engagement, the syringe needle 34 is formed within the chamber 12 and attached to the supporting body 24, for axially centering support of the needle within the hollow chamber and in turn is securely mounted to an inner or proximal end of the needle 34, a distal end 40, of the needle 34, adapted for injection in a patient for serving to pass the fluid to be injected 26, which is then received from the hollow chamber 12, to pass thru the needle 34, into the patient, an annular projection 38, disposed about the tubular coupling 32, to engage the distal end of the needle when it is withdrawn into the chamber 12, and a snap-socket fastener arrangement 50, consisting of one receiving-female portion 52, and one snap-fit-engaging male portion 54, forming a pressure sensitive fastening thereto. Either the one or the other portions 52, or 54, included on an end of the piston proximal the support body, and the other remaining of the one or the other portions included on an end of the support body 24, proximal the piston; and also the method of the construction thereof.

The invention relates further to a method of making a disposable singly usable medical syringe within the disclosure thereof as more particularly described herein.

2. Description of the Prior Art

Various prior art safety medical syringes, and syringe needle disablers and like systems, as well as apparatus and method of their construction in general, are found to be known: and exemplary of the U.S. prior art are the following:

| | |
|---|---|
| Jennings | 4,650,468 |
| Braginetz | 4,883,471 |
| Braginetz | 4,888,002 |
| Magre | 4,932,939 |
| Straw | 4,985,021 |
| Dillard | 5,057,086 |
| Narayanan | 5,057,088 |
| Dyke | 5,059,184 |
| Gaarde | 5,064,419 |

Straw, Dillard and Dyke, disclose a complex spring-loaded sheathing, to cover a used or contaminated needle.

Braginetz '471 describes a syringe that retracts the contaminated needle into the syringe body through a careful alignment of a system of vent holes.

Braginetz '002, as well as Jennings and Magre, disclose; a selectively connected needle being withdrawn Into a body of the syringe after use, and one requiring the use of two hands to operate the screw-type engagement.

Straw, noted above shows a sleeve or sheath fitted to cover a contaminated needle.

Narayanan, shows a movable sheath for the syringe needle.

Gaarde, describes a self-shielding syringe incorporating a spring that thrusts the needle forceably back into a receiving cylinder after the cylinder's covering membrane is punctured by the needle.

These patents or known prior uses teach and disclose various types of medical syringes and the like of various sorts and of various manufactures as well as methods of their construction, but none of them whether taken singly or in combination disclose the specific details of the combination of the invention, including but not limited to the automatic needle withdrawing operation, in such a way, as to bear upon the claims of the present invention.

SUMMARY OF THE INVENTION

An object, advantage and feature of the invention is to provide a disposable, singly-usable medical syringe 10, wherein after its use for injecting serum into a patient by a doctor-technician, the needle 34, is automatically attached and withdrawn into and latched in the interior body hollow chamber 12, of the syringe 10, for preventing unintended and unprofessional uses and unintended needle sticking injuries.

Another object of the invention is directed further to providing a disposable medical syringe 10, comprising a hollow syringe chamber 12, for receiving a piston 14, traversing a displaceable extendible path 16, in the chamber, a rod 18, axially coupled to one end of the piston 14, and at the other end to a thumb engaging surface 20, which allows a one handed dual pressure operation a stop member 22, in the hollow chamber 12, at a proximal end and adjacent to the rod 18, for limiting at one end the travel of the piston thru the extent of the path 16, a substantially conical cap 30 formed at a distal end of the hollow chamber and having a tubular coupling 32, member for receiving in frictional engagement a syringe needle 34, a surrounding supporting body 24, for axially centering support of the needle within the hollow chamber and securely mounted to an inner end of the needle 34, a distal end of the needle 34, adapted to be slightly off axis angularly biased and adapted in a known manner for fluid injection in order to pass fluid 26, received, by a lesser pressure applied to the piston 14, from the hollow chamber 12, to then pass into the patient; an annular projection 38, disposed about the tubular coupling 32, for engaging the withdrawn distal end of the needle therein, as shown in FIG. 2 at alternate position indicated by 32 a, a snap-socket fastener arrangement 50, consisting of one receiving-female portion 52, and one snap-fit-engaging male portion 54, automatically responsive to a greater pressure on piston 14, fastening thereto, either one or the other of the portions 52, or 54, included on an end of the piston proximal the support body, and the other, of the one or the other portions, releasably included on an end of the support body proximal the piston and fixedly attached to the support body 24, and also the method of the construction thereof.

Another object of the invention is to provide a method of making an automatic, needle disposable, singly-usable medical syringe according to the description of the apparatus as set forth.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF A PREFERRED EMBODIMENT OF THE INVENTION

Figure 1:
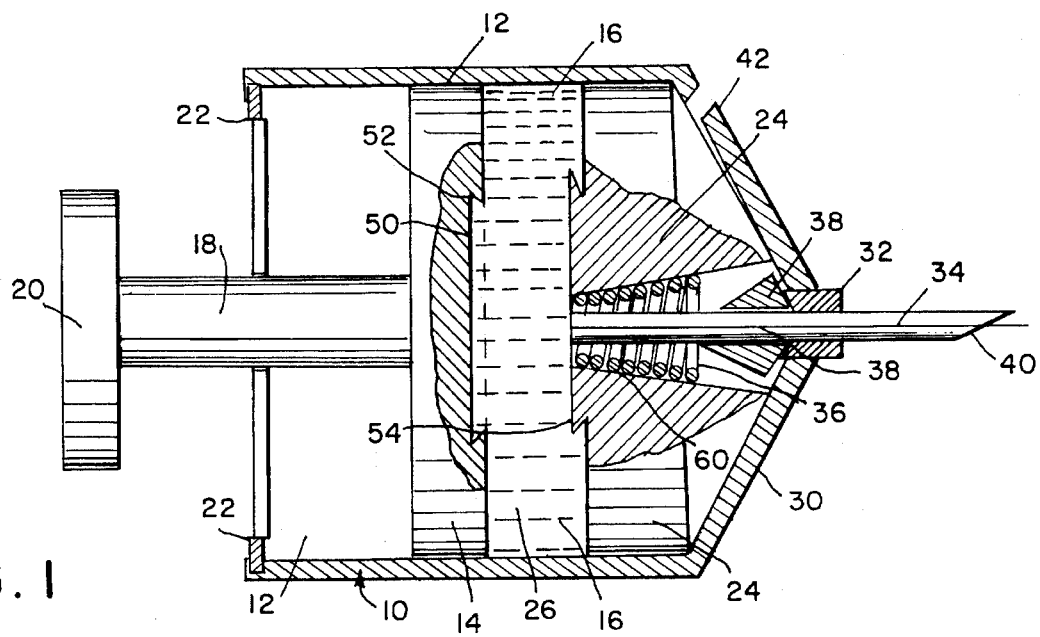
FIG. 1 is an elevation view of a disposable and singly-usable medical syringe and illustrating a typical installation of the system according to a preferred embodiment and best mode of the present invention.
Figure 2:
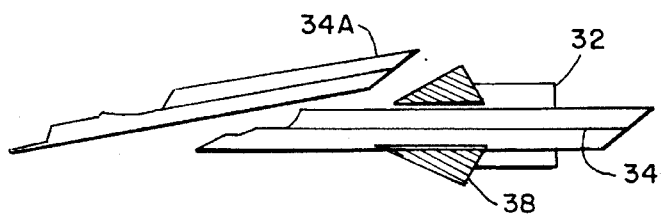
FIGS. 2 and 3 are cross sectional stylized views of a detail of the disposable and singly-usable medical syringe of FIG. 1, showing the needle withdrawn within the tubular body and also (FIG. 3) with a biased base to engage the needle to trap it in the annular projection 38.

Referring now to the drawings there is shown in the figure a disposable medical syringe 10, consisting of a hollow syringe chamber 12, for receiving a piston 14, traversing a displaceable extendible path 16, in the chamber.

A rod is 18, axially coupled to one end of the piston 14, and at the other end to a thumb engaging surface 20 and a stop member 22, in the hollow chamber 12, is positioned at a proximal end and adjacent to the rod 18, for terminating one end of the travel of the displaceable extendible path 16.

A cap 30, is securely formed at a distal end of the hollow chamber from the one end and having a tubular coupling 32, for receiving in frictional engagement a syringe needle 34, and a supporting body for axially centering support of the needle is positioned within the hollow chamber and securably mounted to an inner end of the needle 34.

A distal end 40, of the needle 34, is adapted for injection in a patient for serving to pass fluid 26, received from the hollow chamber to pass into the patient, an annular projection 38, disposed about the tubular coupling 32, for engaging the distal end of the needle when it is withdrawn into the body 12, in response to the angular bias of the needle 34 therein.

The drawing shows the relative displacements of the piston and directions for movement of the piston 14, for:

(1) readying the syringe for Intake of serum, by expelling the air in the chamber 12, by making a "forward stroke" of the plunger to make a place for the fluid or serum, (2) to fill the cavity of the syringe with fluid or serum, when the distal end of the needle is inserted in a fluid or serum, by a "reverse stroke"

(3) dispensing by a second "forward stroke," with normal pressure on the thumb engaging surface and Injecting the serum when the distal end of the needle is disposed in a patient, (4) the direction of displacing the piston 14, with extra pressure on the thumb engaging surface to automatically access the latch by the snap-socket fastener 50, and (5) to withdraw the needle 34, and its surrounds 36 and 24, into the chamber for the needle 34, having its bias freed to engage the projection 38.

Figure 3:
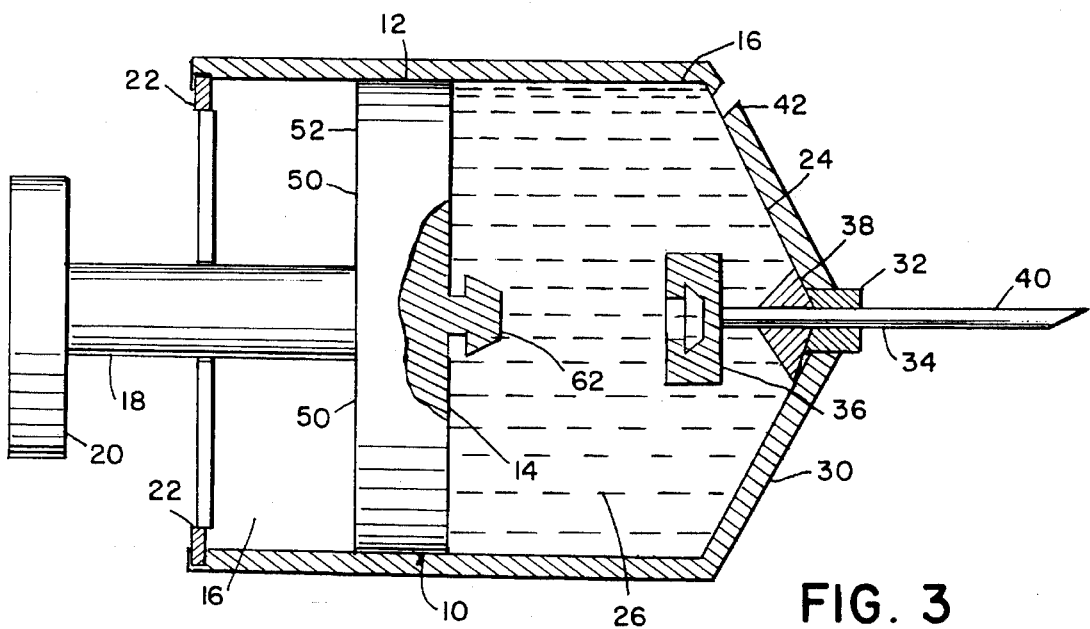

A snap-socket fastener arrangement 50, consisting of one receiving female portion 52, and one snap-fit-engaging male portion 54, which may be angularly skewed, and a pressure responsively automatically matingly fastening thereto and withdrawing the needle 34, on an angular bias as shown in FIG. 3. Either the one or the other of said portions included on an end of the piston proximal the support body, and the other of the one or the other portions included on an end of the support body proximal the piston.

The projection 38, retains the distal end of the needle 34, by means of a biasing tension spring 60, or like skewed barb engaging member 62, FIG. 3, or by essentially equivalent means such as a magnetized component in or integral with the projection 38, for being attractive to material such as steel in the needle 34.

A vent hole 42, is opened in the hollow chamber 12 to allow the joined male portion 52, and female portion 54, of the snap fastener 50, when joined to withdraw with the needle 34, its tubular coupling 36, and its supporting body 24, and plunger 14, all moving in unison away from the cap portion 30, of the syringe 10. The snap fastener 50, may comprise an annular cup receptor 54, and an annular barb member 52. Alternatively the projection 38, about the tubular coupling 32, is eccentrically magnetically attractive to the steel needle or a tension spring 60, or a slight alignment bias of the tubular coupling 36, at the base of the needle generally biases the distal end of the needle, when released into the chamber 12 in to the annular projection 38 to prevent any reuse or reextension of the needle for improper or normal purposes.

The apparatus of the disposable medical syringe 10 of the invention may be so constructed and arranged in its component parts that it may be assembled as a kit or in kit form.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the Invention.

What is claimed is:

1. A safely-disposable, singly-usable medical syringe comprising a) a hollow chamber, having a first end and a second end;

b) a piston, within said chamber, for traversing a displaceable extendible path in said chamber, having a first side facing the first end of said chamber, having a second side facing the second end of said chamber, where said second side of said piston further includes a first portion of a snap-socket fastener arrangement facing said second end of said chamber;

c) a rod, having a first end and a second end, where said first end is axially coupled to the first side of said piston;

d) a thumb-engaging surface, coupled to the second end of said rod;

e) a stop member, formed in the first end of said chamber and adjacent to said rod for terminating one end of the displaceable extendible path;

f) a substantially conical cap, removeably mounted to the second end of said chamber, having a vent opening in said cap for allowing said piston to traverse said chamber;

g) a hollow needle, having a first end and a second end, where said second end is adapted for injecting a fluid into a patient;

h) a tubular coupling, mounted in said cap for receiving in frictional engagement said needle along an axis;

i) an annular projection, within said chamber and tubularly coupled to said tubular coupling; and j) a support body, within said chamber, having a first side securely mounted to the first end of said needle at a slight angular bias to said needle axis, having a second side facing said second side of said piston where said second side of said support body further includes a second portion of said snap-socket fastener arrangement which faces said first portion of said snap-socket fastener arrangement so that when said first portion of said snap-socket fastener arrangement is engaged with said second portion of said snap-socket fastener arrangement and said needle is drawn into said chamber said slight angular bias created by said support body causes said needle to move from its axis and disengage from said annular projection thereby trapping said needle within said hollow chamber.

2. The device of claim 1, wherein said snap-socket fastener arrangement is comprised of an annular-cup receptor and an annular barb member.

3. The device of claim 2, wherein said needle is comprised of steel.

4. The device of claim 3, wherein said tubular coupling is magnetically attractive to steel.

5. The device of claim 4, wherein said support body further includes a tension spring which angularly biases said needle.

6. The device of claim 5, wherein said cap is removably mounted to the second end of said chamber.

7. The device of claim 1, wherein said needle is comprised of steel.

8. The device of claim 7, wherein said tubular coupling is magnetically attractive to steel.

9. The device of claim 1, wherein said support body further includes a support body which angularly biases said needle.

10. The device of claim 1, wherein said cap is removably mounted to the second end of said chamber.

* * * * *